United States Patent [19]
Ebel et al.

[11] Patent Number: 5,568,715
[45] Date of Patent: Oct. 29, 1996

[54] AUTOMATED INSPECTION SYSTEM WITH TRANSPORT AND EJECTOR CONVEYOR

[75] Inventors: James A. Ebel; Michael F. Widman, both of Jacksonville, Fla.

[73] Assignee: Johnson & Johnson Vision Products, Inc., Jacksonville, Fla.

[21] Appl. No.: 251,474

[22] Filed: May 31, 1994

[51] Int. Cl.⁶ ............................ B65B 57/10; G01N 21/90
[52] U.S. Cl. ................................................. 53/54; 53/494
[58] Field of Search .......................... 53/54, 53, 52, 53/498, 495, 494, 493; 209/509, 936, 939

[56] References Cited

U.S. PATENT DOCUMENTS

| | | | |
|---|---|---|---|
| 4,245,243 | 6/1981 | Gutjahr et al. | 358/106 |
| 4,307,555 | 12/1981 | Mlodozeniec et al. | 53/53 |
| 5,040,353 | 8/1991 | Evans et al. | 53/54 |
| 5,080,839 | 1/1992 | Kindt-Larsen | 264/206 |
| 5,081,816 | 1/1992 | Cardinali | 53/54 |
| 5,442,892 | 8/1995 | Burns, III et al. | 53/54 X |

FOREIGN PATENT DOCUMENTS

| | | | |
|---|---|---|---|
| 070252A1 | 1/1983 | European Pat. Off. | B65B 57/00 |
| 193786 | 9/1986 | European Pat. Off. | G01N 21/90 |
| 2924428 | 12/1980 | Germany | 53/54 |
| 2133873 | 8/1984 | United Kingdom | G01N 21/90 |

*Primary Examiner*—James F. Coan

[57] ABSTRACT

An automated inspection system for inspecting packages, such as blister packages, to verify the presence therein of products, such as contact lenses, prior to heat sealing of the blister packages. The automated inspection system includes a transport and ejector mechanism for ejecting any defective packages determined by the automated inspection system not to have a product therein. The automated inspection system includes an optical inspection station at which packages are optically inspected by video cameras to verify that a product is, in fact, present in each package base. A package conveyor system is provided for conveying the packages by the optical inspection station. Following the optical inspection station, an ejector ramp of the transport and ejector mechanism is selectively switchable between a first raised position in which package bases are passed on for further processing, and a second lowered position in which defective packages are transferred from the package conveyor system to the ejector ramp and a buffer area for ejected packages.

21 Claims, 5 Drawing Sheets

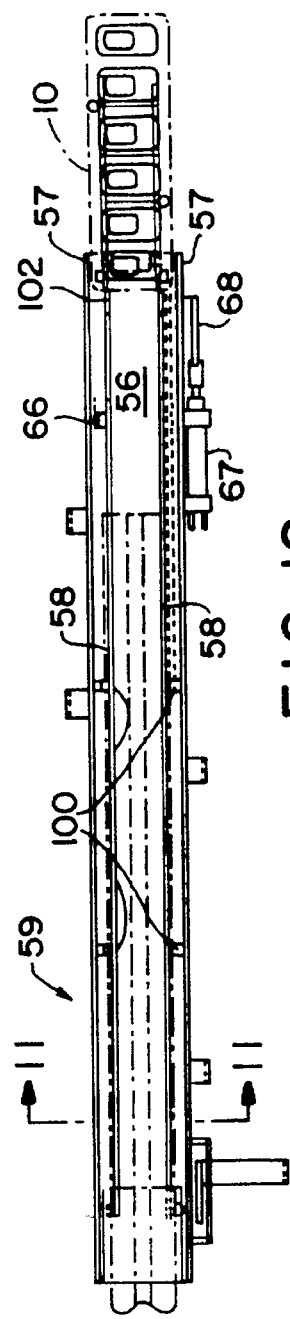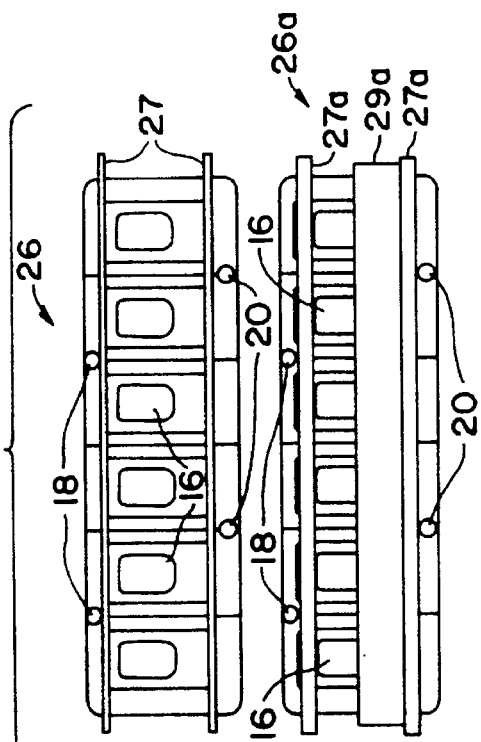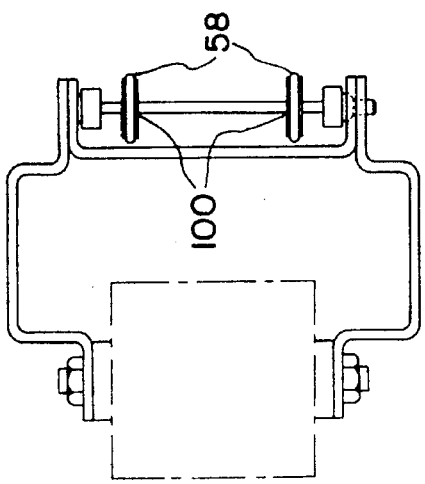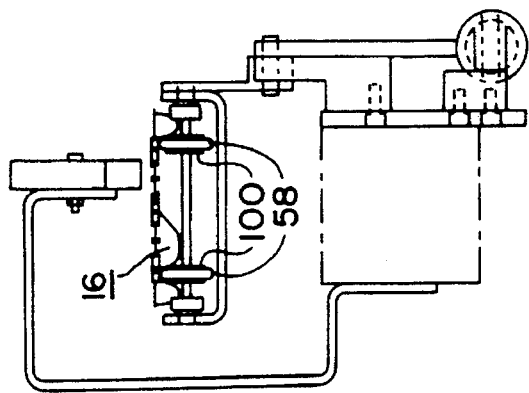

AUTOMATED INSPECTION SYSTEM WITH TRANSPORT AND EJECTOR CONVEYOR

BACKGROUND OF THE INVENTION

1. Field of the Invention

The present invention relates generally to an automated inspection system for inspecting packages to verify the presence therein of a product being packaged, such as a contact lens. The automated inspection system includes a transport and ejector conveyor for ejecting any defective packages determined by the automated inspection system not to have a product therein.

More particularly, the subject invention pertains to an automated inspection system for blister packages to verify the presence therein of contact lenses prior to heat sealing of the blister packages on subsequent manufacturing lines. The automated inspection system and the transport and ejector conveyor prevent defective empty blister packages from reaching customers, and also reduce inspection costs. The system is designed to identify and reject all blister packages with missing lenses and present them to an operator for rework.

2. Discussion of the Prior Art

Recently, several automated systems have been developed for producing ophthalmic lenses, particularly contact lenses, and, for example, one such system is disclosed in U.S. Pat. No. 5,080,839. These systems have achieved a very high degree of automation, and the lenses may be molded, removed from the molds, further processed and packaged all without any direct human involvement. Even with these highly automated systems, however, normally after the lenses are packaged, each package is visually inspected by a person to verify that the package contains a lens, which represents a significant cost. The cost of package inspection could be substantially reduced if the inspection were automated. In addition, although these personal inspections are highly accurate, the reliability of the package inspection could be made even more accurate by employing an automated inspection to verify the presence of lenses in packages.

Automated loading of lenses without verifying an actual transfer of a contact lens into a package base can result in more than two percent of processed packages without a lens, which is more than ten times the average rate found on one production line which uses manual loading of lenses. The present invention concerns an automated inspection vision system which detects package bases having missing lenses, greatly minimizing this error.

SUMMARY OF THE INVENTION

Accordingly, it is a primary object of the present invention to provide an automated inspection system for inspecting packages to verify the presence therein of a product being packaged, such as a contact lens. The automated inspection system includes a transport and ejector conveyor for ejecting any defective packages determined by the automated inspection system not to have a product therein.

A further object of the subject invention is the provision of an automated system for inspecting blister packages to verify therein the presence of contact lenses prior to heat sealing of the blister packages.

Another object of the present invention is to provide a transport and ejector mechanism for an automated inspection system which inspects lens packages automatically at a rate of about 12 packages per minute to verify, with an error rate of less than 1% for both type I (false reject) and type II (passed reject) errors, and preferably a false-reject error rate of less than 0.1% that lenses are, in fact, in the packages.

In accordance with the teachings herein, the present invention provides an automated inspection system having a transport and elector conveyor. The automated inspection system includes an optical inspection station at which package bases, having a product such as a contact lens therein, are optically inspected to verify that a product is, in fact, present in each package base. A package conveyor system is provided for conveying the package bases by the optical inspection station. Following the optical inspection station, an ejector mechanism is selectively switchable between a first position in which package bases are passed on for further processing, and a second position in which the ejector system transfers packages that are determined by the optical inspection station not to have a product therein from the package conveyor system to an ejector buffer area.

In greater detail, the package bases comprise linear arrays of connected individual package bases, each of which is to receive a product therein. The optical inspection station includes a plurality of video cameras, each of which optically inspects a given number of individual package bases less than the number of package bases in the linear array. The optical inspection station includes an illumination fixture mounted on one side of the package conveyor system, and video cameras mounted on an opposite second side of the package conveyor system. The video cameras are mounted on a support which is independently adjustable by separate x, y and z adjustor mechanisms for translation along x, y and z axes to precisely position the video cameras relative to the package conveyor system. In a disclosed embodiment, each linear array of connected package bases comprises six connected package bases, and the optical inspection station includes three cameras placed in a series along the package conveyor system. Each video camera optically examines an adjacent two connected package bases, such that the three video cameras simultaneously optically examine all six connected package bases in each linear array.

The package conveyor system includes an endless conveyor which travels in an endless loop by 1) a package base depositing station at which package bases are deposited onto the package conveyor system, 2) a product depositing station at which products are deposited into each package base, 3) the optical inspection station at which the packages are optically inspected to verify that each package base has a product deposited therein, and 4) the ejector system.

The ejector system includes an ejector conveyor system, and an ejection ramp which is raised or lowered onto the package conveyor system. A pneumatic cylinder drives the ejection ramp between raised and lowered positions. The ejector conveyor system includes an endless belt transport for transporting ejected packages up the ejection ramp to a buffer area on which ejected packages are accumulated.

The package conveyor system includes spaced rails upon which the packages slide during movement along the package conveyor system. The packages define a product receiving cavity, and the spaced rails include two spaced rails which are positioned on opposite sides of the product receiving cavity. The packages also define first alignment lugs depending from a first end of the package adjacent to and slightly spaced from the product receiving cavity, and one rail is positioned between the first depending lugs and the product receiving cavity. Second alignment lugs are provided depending from a second end of the package which ride along the second rail. Each of the rails is preferably rounded along its top edge to accommodate sliding of the packages therealong. The package conveyor system further includes a belt drive having drive lugs periodically spaced along the belt drive, which drive the packages along the spaced rails. The package conveyor system is periodically driven to index and stop the packages at periodically spaced positions along the package conveyor system, at which the functions described herein are performed.

BRIEF DESCRIPTION OF THE DRAWINGS

The foregoing objects and advantages of the present invention for an automated inspection system with a transport and ejector conveyor may be more readily understood by one skilled in the art with reference being had to the following detailed description of several preferred embodiments thereof, taken in conjunction with the accompanying drawings wherein like elements are designated by identical reference numerals throughout the several views, and in which:

FIGS. 8 and 9 are respectively a front elevational view and a section view, taken along arrows 9—9 in FIG. 8, of a transport and ejector mechanism pursuant to the subject invention;

FIGS. 10 and 11 are respectively a top plan view and a sectional view, taken along arrows 11—11 in FIG. 10, of the transport and ejector mechanism illustrated in FIGS. 8 and 9; and FIG. 12 illustrates bottom plan views of two embodiments of a transport conveyor belt positioned beneath a blister package as shown in FIG. 1, illustrating the positioning of the transport conveyor belt relative to the alignment lugs and the product cavity of the blister package.

DETAILED DESCRIPTION OF THE DRAWINGS

Figure 1:
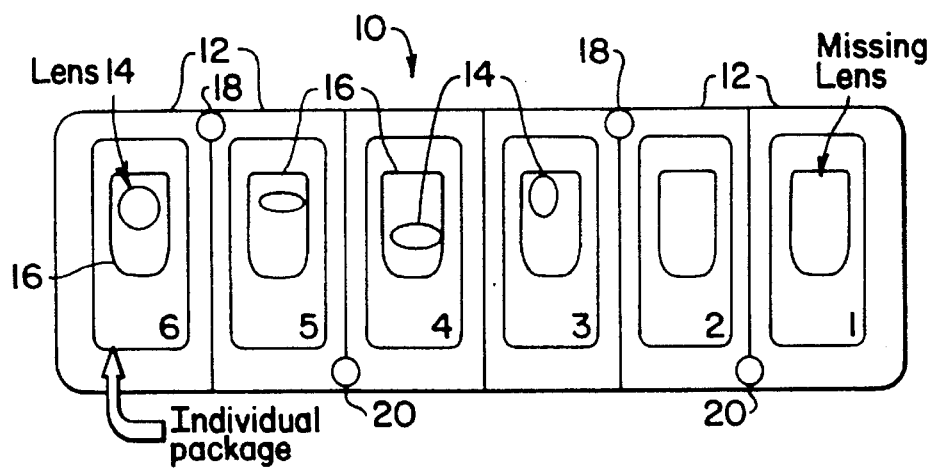
FIG. 1 is a schematic top planar view of a blister package comprising a linear array of six individual packages, each of which is to be inspected by the automated inspection system to determine if each individual package has a product such as a lens deposited therein.

Referring to the drawings in detail, FIG. 1 is a schematic top planar view of a blister package 10 comprising a linear array of six individual packages 12, each of which is to be inspected by the automated inspection system to determine if each individual package has a product such as a lens 14 deposited therein. If any lens is missing, the entire blister pack is rejected. The packages 10 define a product receiving cavity 16, and further define first alignment lugs 18 depending from a first side of the package adjacent to and slightly spaced from the product receiving cavity, and second alignment lugs 20 depending from a second side of the package. The product cavities are located on 1.8 inch centers. The depths of the product receiving cavities 16 and the first and second alignment lugs 18 and 20 are illustrated generally in FIG. 9. With the blister package shown in FIG. 1, lenses are disposed in the cavities of packages, however some lenses may be missing from some of the packages, as illustrated by FIG. 1.

Figure 4:
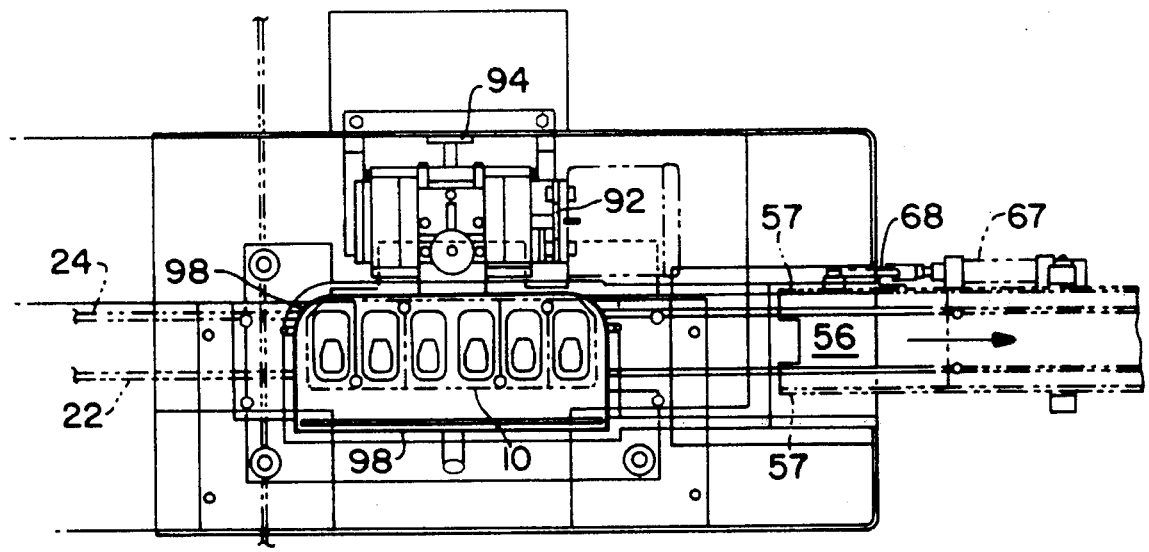
FIG. 4 is a top plan view, taken from the rear, of an automated inspection system and transport and ejector system of the subject invention.
Figure 6:
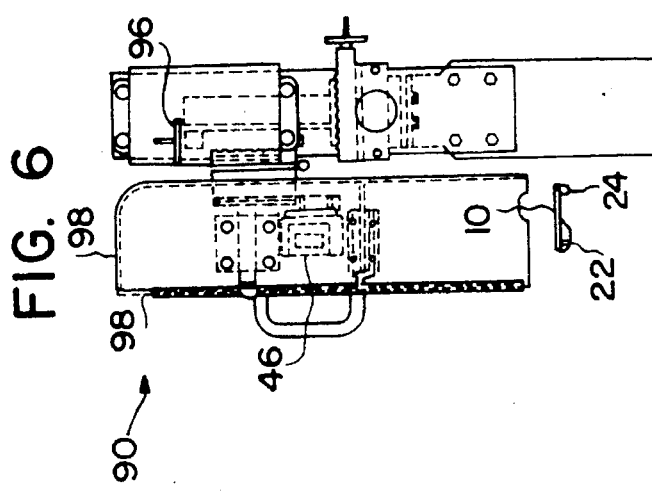

The packages are transported through the automated inspection system by sliding on first and second spaced transporter steel rails 22 and 24. As illustrated in FIGS. 4 and 6, the arrangement is such that a first rail 22 is positioned between the first alignment lugs 18 and the product receiving cavity 16, and the second rail 24 is positioned adjacent to the second alignment lugs.

Figure 2:
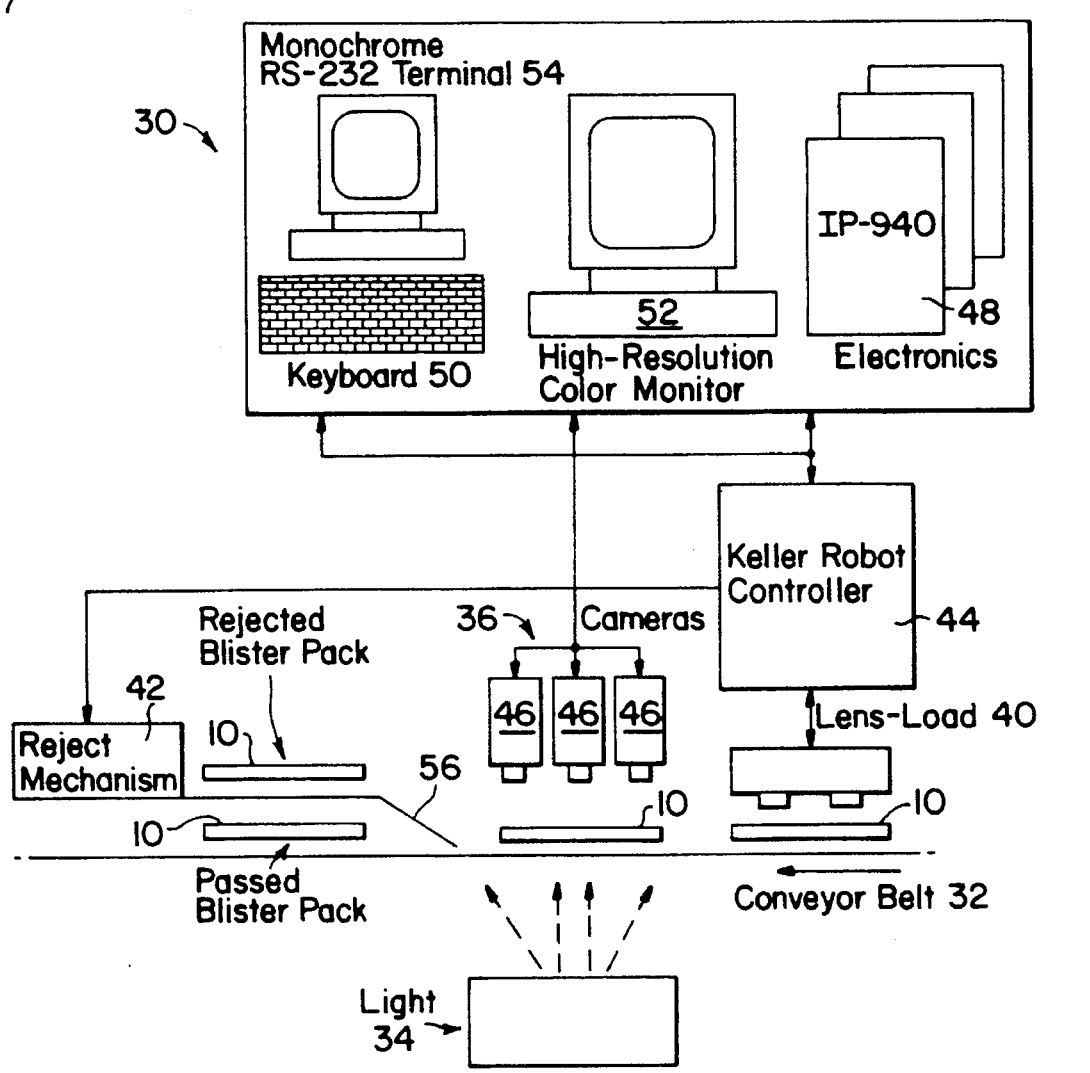
FIG. 2 is a schematic illustration of a lensload vision system employing an automated inspection system having a transport and ejector system pursuant to the subject invention.

FIG. 2 is a schematic illustration of a lensload vision system 30 employing an automated inspection system having a transport and ejector system pursuant to the subject invention. The system 30 generally comprises a transport subsystem 32, an illumination subsystem 34, imaging inspection subsystem 36, and image processing subsystem 38. FIG. 2 also shows a lens loading mechanism or assembly 40, a reject mechanism 42, a reject mechanism controller 44, and a plurality of groups of lens packages 10 in various conveyance positions in FIG. 2.

With a preferred embodiment of the system 30, the transport subsystem 32 includes transporter rails 22 and 24, and an endless package conveyor belt 26. The illumination subsystem 34 includes a housing, a light source and diffuser, as described in greater detail in patent application Ser. No. 08/251,525 (attorney docket 9291), filed May 31, 1994 for Method and System for Inspecting Packages. Also, in a preferred system 30, the imaging subsystem 36 includes a plurality of three cameras 46, each of which includes conventional components of a housing, pixel array, shutter and lens assembly. The inspection station requires three cameras to image a blister pack. A single IP940 image processor acquires images from the three cameras, processes those images to determine if a lens is missing from one of the six blister cavities, and reports the disposition of the blister pack to the reject controller 44. These events take place in 1.25 seconds. The three cameras are preferably configured to make the synchronization circuitry of one camera drive the sync inputs of the other two cameras. This makes the video synchronization from all three cameras identical, and allows the IP940 to switch video inputs between fields with no frame delays.

As shown in FIG. 2, and as described in greater detail in patent application Ser. No. 08/251,525 (attorney docket 9291), filed May 31, 1994 for Method and System for Inspecting Packages, the image processing subsystem 38 includes a plurality of processing and memory boards 48, input means such as a keyboard 50, video monitor 52 and an RS-232 terminal 54. In the schematic representation of FIG. 2, the packages 10 are transported through the lensload station 40, in which a contact lens is loaded into each cavity 16, then through the optical inspection terminal 36, at which the presence is verified of a lens in each package, then through an ejector mechanism 42, at which defective packages, not having a contact lens loaded therein, are removed from a package conveyor belt 26.

The lensload vision system (LLVS) includes a high resolution display, three image processors and a terminal, which are linked via overhead cables to a camera module, consisting of three video cameras 46, and a robot controller 44. In less than two seconds, all six packages in a single blister pack are imaged by three cameras, inspected by the LLVS, and the results reported to the robot controller. If the blister pack has a missing lens, it is rejected onto a rework ramp, where a single operator places it into a rework magazine. During a three second or less delay between an inspection result and a conveyor index motion, the robot controller 44 activates a rejection gate 56 if necessary. Illumination for the inspection is provided by a constant light source 34, designed to maximize contrast and uniformity. The system is able to perceive the contrast at the edge of a lens in the package, even though the lens is more transparent than the package.

The success rate was specified to be less than one percent error in either the type I (false reject) or type II (passed reject) categories. This rate ensures that the operator has time to manipulate all rejections. The LLVS more than meets this criteria. During runs, the type I rate was 0.29 percent, and the type II was 0.10 percent. Multiplying the type II rate by 1.45 percent, the typical missing lens rate of the robots, yields a very low total rate of missing lenses passed. In fact, the rate is so low that it virtually eliminates the category of missing lenses. Instead of a normal 1,700 lenses missing per 1,000,000, the LLVS performs at a rate equal to 15 per 1,000,000. Customer satisfaction should be positively affected by the lower rate of missing lenses.

Figure 3:
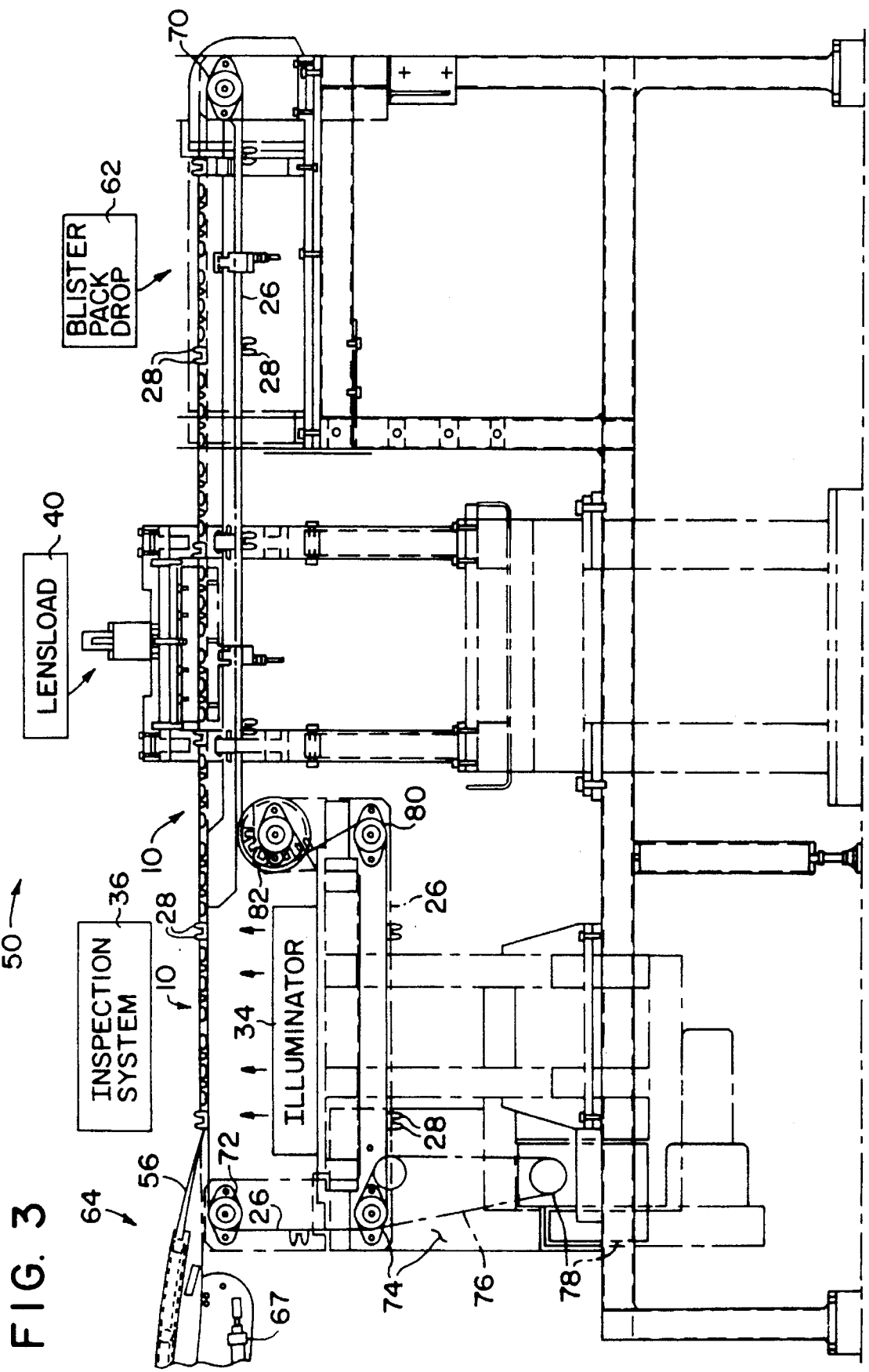
FIG. 3 is a front elevation view of a packaging system having a sequence of a blister package drop machine for placing package bases on a package conveyor system, a lensload machine for placing contact lenses in the blister package bases, an automated inspection system for verifying that each package base does, in fact, have a contact lens deposited therein, and a transport and ejector system for ejecting packages determined by the automated inspection system not to have a contact lens therein, and illustrates the path of a common package conveyor which conveys packages sequentially through all of the machines and systems.

FIG. 3 is a front elevation view of a packaging system 60 having a sequence of a blister package drop machine 62 for placing package bases on a package conveyor system, a lensload machine 40 for placing contact lenses in the blister package bases, an automated inspection system 36 for verifying that each package base does., in fact, have a contact lens deposited therein, and a transport and ejector system 64 for ejecting packages determined by the automated inspection system not to have a contact lens therein.

Various lens load mechanisms 40 are known in the art. Commonly, these lens load mechanisms include a robot, a robot arm, sometimes referred to as a robot cell, that is used to carry lenses from a supply or source thereof and to deposit those lenses in the cavities of packages. The packaging system 60 may be used independent of any specific method or apparatus placing or depositing lenses in the packages. The system 60 is well suited., though, for use in a larger system in which lenses are automatically made, inspected, treated, and then placed in packages by robots. Immediately after a robotics lens loading operation, the blister pack transport belt is indexed one position, moving a filled blister pack further down the line. After two index movements, the blister pack arrives beneath the LLVS camera module. Inside the module, three cameras 46 image the blister pack, two packages per camera.

The package conveyor system includes an endless conveyor belt 26 which travels in an endless loop by 1) the package base depositing station 62 at which package bases are deposited onto the package conveyor system 26, 2) the product depositing station 40 at which products are deposited into each package base, 3) the optical inspection station 36 at which the packages are optically inspected to verify that each package base has a product deposited therein, and 4) the transport and ejector system 64.

The transport and ejector system 64 includes an ejection ramp 56, which is pivoted about point 66, and is actuated by a pneumatic cylinder 67 operating through an L-shaped crank 68, pivoted about pivot 69, and an arm 71, to raise or lower the ramp 56. In a raised position, the packages on the package conveyor 26 proceed under the ramp 56 for further processing. In a lowered position, the packages on the package conveyor proceed up the ramp 56 where they are driven by an endless conveyor, comprised of two O-ring rubber belts 58 on opposite sides of the ramp 56. The drive belts 58 engage the package and transfer it to a buffer area 59 where the packages are accumulated.

The package conveyor system includes spaced rails 22, 24 upon which the packages slide during movement along the package conveyor system. The first rail 22 is positioned between the first alignment lugs 18 and the product receiving cavity 16, and the second alignment lugs 20 ride along the second rail 24. Each of the rails is preferably rounded along its top edge to accommodate sliding of the packages therealong. The package conveyor system further includes an endless conveyor belt 26 having drive lugs 28 periodically spaced along the belt drive, which drive the packages along the spaced rails. The package conveyor system is periodically driven to index and stop the packages at periodically spaced positions along the package conveyor system, at which the functions described herein are performed.

FIG. 12 illustrates bottom plan views of two embodiments 26 and 26a of a transport conveyor belt positioned beneath a blister package a shown in FIG. 1, illustrating the positioning of the transport conveyor belt relative to a product cavity 16 of the blister package 10. The drive belt 26 should not interfere with the operation of the optical inspection system 36 in which light from an illumination source 34 illuminates the bottom Of a blister package 10, and cameras 46 image the light transmitter through the blister package 10 for processing to determine if a contact lens 14 is present in each of the six product cavities 16. Accordingly, each drive belt 26 or 26a comprises spaced belts 27 or 27a, one positioned on each side of the product cavity 16, and possibly a reinforced section 29a. The spaced belts 27 or 27a provide an opening therebetween to allow optical inspection of the product cavities 16 of the blister package 10.

Starting at the upper right corner of FIG. 3, the endless conveyor belt 26 travels 180° around an idler pulley 70, then travels oh the rails 22, 24 to the left under the blister pack drop 62, the lensload 40, the optical inspection station 36, and the ejector mechanism 64, travels 90° around idler pulley 72 down to drive pulley 74, travels 90° around drive pulley 74 (which is driven by a further drive belt 76 and motor 78) to idler pulley 80, then upwardly through idler pulley 82, which is constructed with a gap opening in its face to pass the drive lugs 28, and then to the right back to idler pulley 70.

The optical inspection station 36 includes a plurality of three video cameras 46, each of which optically inspects a given number (e.g., two) of individual package bases less than the number of package bases in the linear array. The optical inspection station includes an illumination fixture 34 mounted on one side of the package conveyor system, and video cameras 46 mounted on an opposite second side of the package conveyor system. The presence of a blister package 10 at the optical inspection system 36 is verified by an optical probe 37, FIG. 5, positioned underneath the position of a blister package 10 stopped at the optical inspection system.

Figure 5:
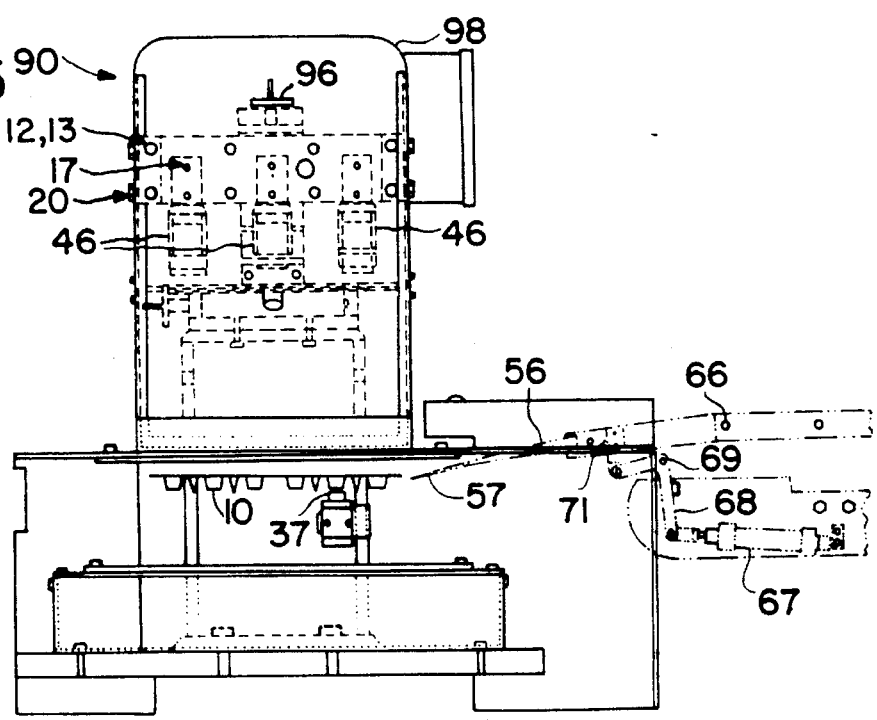
FIGS. 5, 6 and 7 are respectively rear elevational, right side elevational, and top plan views of an inspection camera cell pursuant to the present invention.
Figure 7:
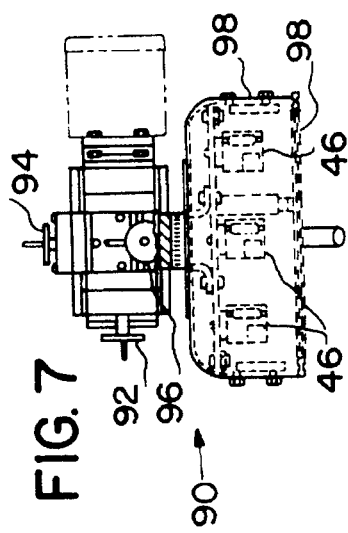

FIGS. 5, 6 and 7 are respectively rear elevational, right side elevational, and top plan views of an inspection camera cell 70 pursuant to the present invention. Any suitable camera or cameras may be used, for instance, each camera 46 may be a Panasonic GP-MF552 black and white CCD camera. The camera outputs images in an RS-170 mode, with 2-line interlace. Only one of the line interlace frames is grabbed by the image processor 38 input in order to limit the image size to under 200,000 pixels. Keeping the total image size under this threshold is helpful in sizing the required memory of the processor board, thereby limiting the cost of the system.

FIGS. 5, 6 and 7 are respectively rear elevational, right side elevational, and top plan views of an inspection camera cell 90 pursuant to the present invention. In a disclosed embodiment, each linear array of connected package bases comprises six connected package bases, and, referring to FIGS. 5, 6 and 7, the inspection camera cell 90 includes three video cameras 46 placed in a series along the package conveyor system. Each video camera optically examines an adjacent two connected package bases 12, such that the three video cameras simultaneously optically examine all six connected package bases in each linear array.

The video camera cell 90 is mounted on a support which is independently adjustable by separate x, y and z adjustor mechanisms for translation along x, y and z axes to precisely position the video cameras relative to the package conveyor system. The x adjustment mechanism includes a bell crank 92 which turns a lead screw to move the cameras in an x direction, along the direction of movement of the conveyor. The y adjustment mechanism includes a second bell crank 94 which turns a lead screw to move the cameras in an y direction, across the width of the blister package. The z adjustment mechanism includes a third bell crank 96 which turns a lead screw to move the cameras in an z direction, in a vertical direction as illustrated in FIG. 5. The enclosure 98 for the three cameras in cell 90 is generally light tight to minimize illumination noise from background illumination.

Figure 8:
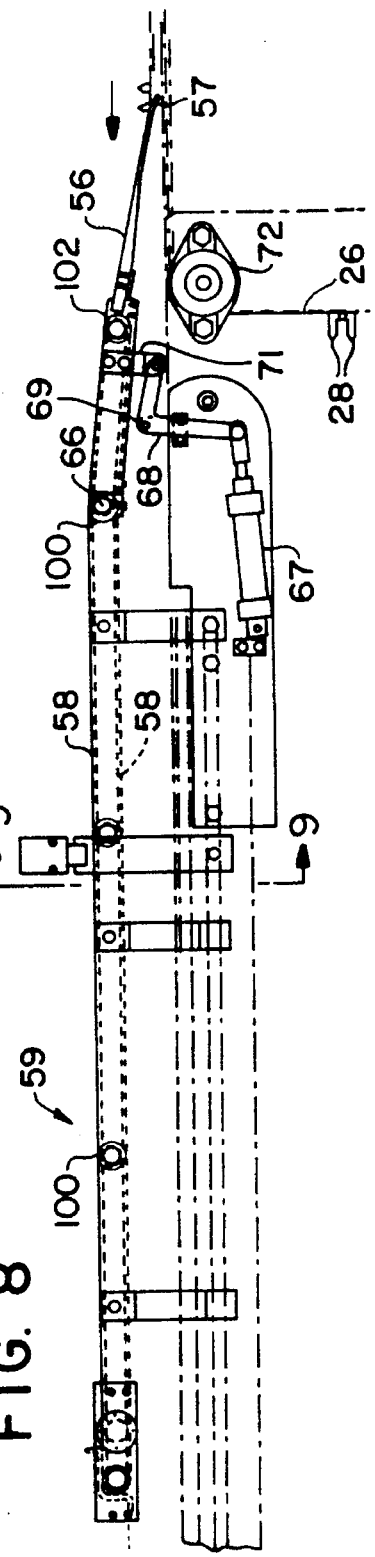

FIGS. 8 and 9 are respectively a front elevational view and a section view, taken along arrows 9—9 in FIG. 18, of a transport and ejector mechanism 64 pursuant to the subject invention. FIGS. 10 and 11 are respectively a top plan view and a sectional view, taken along arrows 11—11 in FIG. 10, of the same transport and ejector mechanism illustrated in FIGS. 8 and 9.

Referring to FIGS. 8–11, the transport and ejector system 64 includes an ejector ramp 56, pivoted about 66. The ejector ramp 56 includes two spaced fingers 57 which are raised or lowered onto the transport rails 22, 24. A conveyor system for the ejector ramp includes two spaced O-ring drive belts 58, traveling along and around idler rollers 100 to an end idler roller 102, at which the drive belts 58 initially pick up the ejected packages 10 being pushed up the two fingers 57 by drive lugs 28 on the package conveyor 26. The ejected packages are then advanced by the O-ring belts 58 to a package buffer area 59 at which the packages are accumulated until an operator retrieves them for rework.

While several embodiments and variations of the present invention for an automated inspection system with a transport and ejector conveyor are described in detail herein, it should be apparent that the disclosure and teachings of the present invention will suggest many alternative designs to those skilled in the art.

What is claimed is:

1. A transport and ejector conveyor for an automated inspection system comprising:
   a. an optical inspection station at which a package array comprising connected individual package bases, each base having a product therein, is optically inspected to verify that the product is present in each package base;
      i. wherein the optical inspection station comprises a plurality of video cameras, each of which optically inspects a given number of package bases;
      ii. wherein the video cameras are mounted on a support which is independently adjustable by separate x, y and z adjustor mechanisms for translation along x, y and z axes to precisely position the video cameras relative to the package bases;
   b. a package conveyor system for conveying the package bases by the optical inspection station;
   c. an ejector system, selectively switchable between a first position in which the package bases are passed on the package conveyor system by the ejector system and a second position in which the ejector system transfers packages that are determined by the optical inspection station not to have a product therein from the package conveyor system to the ejector system.

2. A transport and ejector conveyor for an automated inspection system as claimed in claim 1, wherein said ejector system further comprises an ejection ramp which is raised or lowered onto the package conveyor system.

3. A transport and ejector conveyor for an automated inspection system as claimed in claim 1, wherein the package conveyor system includes a belt drive having drive lugs periodically spaced along the belt drive, and wherein the spaced drive lugs drive the packages along the spaced rails upon which the packages slide during movement along the package conveyor system.

4. A transport and ejector conveyor for an automated inspection system as claimed in claim 1, wherein the package conveyor system is periodically driven to index and stop the packages at periodically spaced positions along the package conveyor system.

5. A transport and ejector conveyor for an automated inspection system as claimed in claim 1, wherein each linear array of connected package bases comprises six connected package bases, and said optical inspection station includes three video bases, and said optical inspection station includes three video cameras placed in a series along the package conveyor system, and wherein each video camera optically examines an adjacent two connected package bases, and the three video cameras simultaneously optically examine all six connected package bases in each linear array.

6. A transport and ejector conveyor for an automated inspection system as claimed in claim 5, wherein at the optical inspection station an illumination fixture is mounted on one side of the package conveyor system, and the video cameras are mounted on an opposite second side of the package conveyor system.

7. A transport and ejector conveyor for an automated inspection system as claimed in claim 1, wherein said package conveyor system includes an endless conveyor which travels in an endless loop.

8. A transport and ejector conveyor for an automated inspection system as claimed in claim 7, wherein said endless conveyor travels in an endless loop by a package base depositing station at which package bases are deposited onto the package conveyor system, a product depositing station at which products are deposited into each package base, and said optical inspection station at which the packages are optically inspected to verify that each package base has a product deposited therein, and said ejector system is positioned adjacent to said package conveyor system after the optical inspection system.

9. A transport and ejector conveyor for an automated inspection system as claimed in claim 7, wherein the endless conveyor includes an endless drive belt having drive lugs periodically spaced along the drive belt, and wherein the spaced drive lugs drive the packages along spaced rails upon which the packages slide during movement along the package conveyor system.

10. A transport and ejector conveyor for an automated inspection system as claimed in claim 7, wherein said endless conveyor travels in an endless loop by a package base depositing station at which package bases are deposited onto the package conveyor system, a product depositing station at which products are deposited into each package base, and said optical inspection station at which the packages are optically inspected to verify that each package base has a product deposited therein, and said ejector system is positioned adjacent to said package conveyor system after the optical inspection system.

11. A transport and ejector conveyor for an automated inspection system as claimed in claim 10, wherein the endless conveyor includes an endless drive belt having drive lugs periodically spaced along the drive belt, and wherein the spaced drive lugs drive the packages along spaced rails upon which the packages slide during movement along the package conveyor system.

12. A transport and ejector conveyor for an automated inspection system as claimed in claim 1, wherein said ejector system comprises an ejector conveyor system.

13. A transport and ejector conveyor for an automated inspection system as claimed in claim 12, wherein said ejector system further comprises an ejection ramp which is raised or lowered onto the package conveyor system.

14. A transport and ejector conveyor for an automated inspection system as claimed in claim 13, wherein said ejector conveyor system includes an endless belt transport for transporting ejected packages up the ejection ramp to a buffer area on which ejected packages are accumulated.

15. A transport and ejector conveyor for an automated inspection system as claimed in claim 13, wherein a pneumatic cylinder drives the ejection ramp between raised and lowered positions.

16. A transport and ejector conveyor for an automated inspection system as claimed in claim 1, wherein the package conveyor system includes spaced rails upon which the packages slide during movement along the package conveyor system.

17. A transport and ejector conveyor for an automated inspection system as claimed in claim 16, wherein the packages define a product receiving cavity, and the spaced rails include two spaced rails which are positioned on opposite sides of the product receiving cavity.

18. A transport and ejector conveyor for an automated inspection system as claimed in claim 17, wherein the packages further define first alignment lugs at a first side of the package adjacent to and slightly spaced from the product receiving cavity, and a first rail is positioned between the first alignment lugs and the product receiving cavity, and second alignment lugs depending from a second side of the package which ride along a second rail.

19. A transport and ejector conveyor for an automated inspection system as claimed in claim 18, wherein the package conveyor system includes a belt drive having drive lugs periodically spaced along the belt drive, and wherein the spaced drive lugs drive the packages along the spaced rails.

20. A transport and ejector conveyor for an automated inspection system as claimed in claim 19, wherein the package conveyor system is periodically driven to index and stop the packages at periodically spaced positions along the package conveyor system.

21. A transport and ejector conveyor for an automated inspection system as claimed in claim 16, wherein each of the rails is rounded along its top edge.

* * * * *